United States Patent [19]

Adams, Jr. et al.

[11] 4,192,669

[45] Mar. 11, 1980

[54] HERBICIDAL ETHERS

[75] Inventors: John B. Adams, Jr., Hockessin; Joel B. Wommack, Jr., Wilmington, both of Del.

[73] Assignee: E. I. Du Pont de Nemours and Company, Wilmington, Del.

[21] Appl. No.: 863,268

[22] Filed: Dec. 22, 1977

[51] Int. Cl.$^2$ .......................... A01N 9/24; C07C 65/02; C07C 69/76
[52] U.S. Cl. ........................................ 71/108; 71/109; 71/116; 260/455 R; 260/501.15; 260/501.17; 260/559 D; 560/62; 562/472; 568/586; 568/637; 568/775
[58] Field of Search ........................... 560/62; 562/472; 71/108, 109, 116; 260/455 R, 501.15, 501.17, 559 D

[56] References Cited

U.S. PATENT DOCUMENTS

| | | | |
|---|---|---|---|
| 3,721,703 | 3/1973 | Nahm et al. | 560/62 X |
| 3,954,442 | 5/1976 | Becker et al. | 560/62 X |
| 4,070,177 | 1/1978 | Nishiyama et al. | 560/62 X |
| 4,070,178 | 1/1978 | Johnson et al. | 560/62 X |

FOREIGN PATENT DOCUMENTS

| | | | |
|---|---|---|---|
| 848526 | 5/1977 | Belgium | 560/62 |
| 2133866 | 1/1973 | Fed. Rep. of Germany | 560/62 |
| 7306625 | 11/1973 | Netherlands | 560/62 |
| 7508016 | 7/1975 | Netherlands | 560/62 |

*Primary Examiner*—Bernard Helfin
*Assistant Examiner*—Vera C. Clarke

[57] ABSTRACT

Ethers, such as 2-[[4-[4-(trifluoromethoxy)phenoxy]phenoxy]]propanoic acid, methyl ester, useful for control of weeds.

27 Claims, No Drawings

HERBICIDAL ETHERS

BACKGROUND OF THE INVENTION

This invention relates to herbicidal ethers.

It is known that the following ethers, inter alia, can be used as herbicides:

| Compound | Patent Reference |
|---|---|
| CF$_3$—⌬—X, Cl | Netherlands 7,508,016 |
| CH$_3$O—⌬—X | U.S. 3,954,442 |
| CF$_3$—⌬—X, NO$_2$ | Belgium 848,526 | where X = 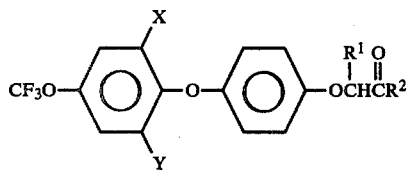

SUMMARY OF THE INVENTION

This invention relates to novel compounds of Formula (I), to agriculturally suitable compositions containing them, and to the method of use of these compounds as herbicides $$CF_3O-⌬-O-⌬-OCHCR^2 \quad (I)$$
(with substituents X, Y on first ring and R$^1$, O, R$^2$ on side chain)

wherein
R$^1$ is H, CH$_3$ or CH$_3$CH$_2$;
R$^2$ is OR$^3$, NR$^4$R$^5$, or SR$^6$;
R$^3$ is H, alkyl of one through six carbons, Na$^\oplus$, K$^\oplus$ ½ Ca$^{+2}$ or $\oplus$NR$^7$R$^8$R$^9$R$^{10}$;
R$^4$ is H, or CH$_3$;
R$^5$ is H, alkyl of one through four carbons or OCH$_3$;
R$^6$ is alkyl of one through six carbons;
R$^7$, R$^8$ and R$^9$ can be the same or different and each can be hydrogen, alkyl of one through four carbon atoms or hydroxyalkyl of two through four carbon atoms;
R$^{10}$ is hydrogen, alkyl of one through twelve carbon atoms or benzyl;
provided that when R$^5$ is OCH$_3$, R$^4$ is CH$_3$;
X is H, Cl, Br or NO$_2$; and
Y is H or Cl;
provided that when Y is Cl, X must be H or Cl.

This invention also relates to novel compounds of Formula II which are useful for the preparation of the compounds of Formula (I).

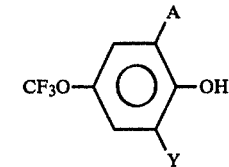

(II)

wherein
A is Cl or Br; and
Y is H or Cl;
provided that when A is Br, Y must be H.

DETAILED DESCRIPTION OF THE INVENTION

Preferred for their high herbicidal activity and/or favorable cost are those compounds of Formula (I) wherein
R$^1$ is CH$_3$; or
R$^2$ is OR$^3$; or
R$^3$ is CH$_3$ or CH$_3$CH$_2$; or
X is H or Cl; or
Y is H.

More preferably R$^1$ to R$^3$, X and Y have the preferred definitions.

Specifically preferred for their higher herbicidal activity and/or more favorable cost are
2-[[4-[4-(trifluoromethoxy)phenoxy]phenoxy]]-propanoic acid, methyl ester and
2-[[4-[2-chloro-4-(trifluoromethoxy)phenoxy]phenoxy]]-propanoic acid, methyl ester.

Depending on exactly which compounds of Formula (I) are being prepared, different preparative methods can be used, as exemplified in the procedures below and explained more fully thereafter:

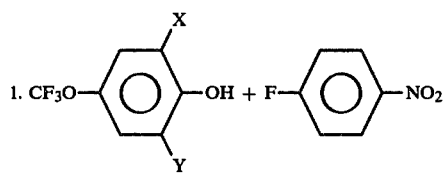

IIa

X is limited to H, Cl and Br
Y=H, Cl, provided when X=Br,
Y must be H

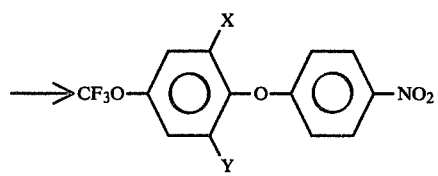

IIIa

X is limited to H, Cl and Br
Y=H, Cl, provided when X=Br,
Y must be H

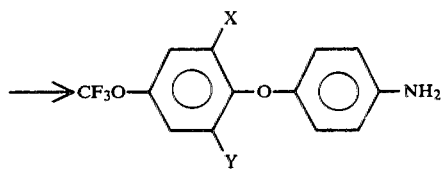

IIIb

X is limited to H, Cl and Br
Y=H, Cl, provided when X=Br,
Y must be H

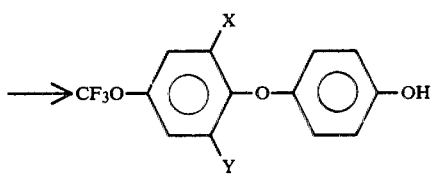

IIIc

X is limited to H, Cl and Br
Y=H, Cl, provided when X=Br,
Y must be H

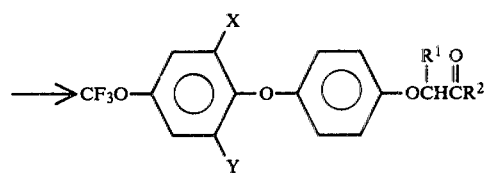

(I)a

X is limited to H, Cl and Br
Y=H, Cl, provided when X=Br,
Y must be H
$R^2$ is $OR^3$, $NR^4R^5$, or $SR^6$, with $R^3$ limited to alkyl of one through six carbons,
$R^1$, $R^4$, $R^5$ and $R^6$ are as defined for (I).

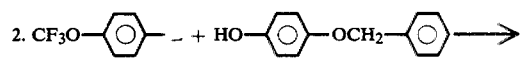

2.  E = Br, I

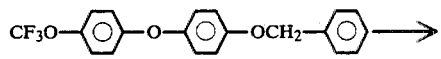

IIIe

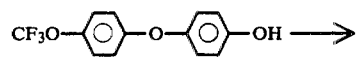

IIId

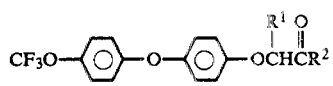

(I)b $R^2$ is $OR^3$, $NR^4R^5$, or $SR^6$, with $R^3$ limited to alkyl of one through six carbons
$R^1$, $R^4$, $R^5$ and $R^6$ are as defined for (I).

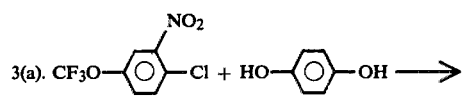

3(a).

—continued

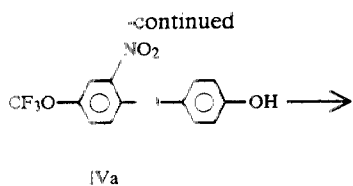

IVa

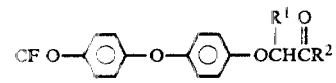

(I)c $R^2$ is $OR^3$, $NR^4R^5$, or $SR^6$, with $R^3$ limited to alkyl of one through six carbons.
$R^1$, $R^4$, $R^5$ and $R^6$ are as defined for (I).

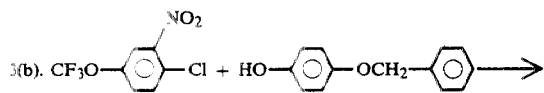

3(b).

IVb

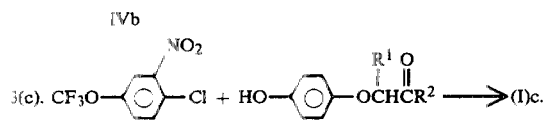

3(c). ⟶ (I)c.

VIa $R^2$ is $OR^3$, $NR^4R^5$ or $SR^6$, with $R^3$ limited to alkyl of one through six carbons
$R^1$, $R^4$, $R^5$ and $R^6$ are as defined for (I).

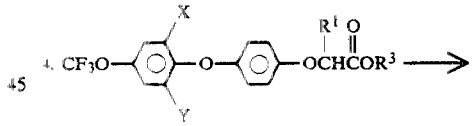

4.

(I)d
$R^3$ is limited to alkyl of 1 through 6 carbons
$R^1$, X and Y are as defined for (I).

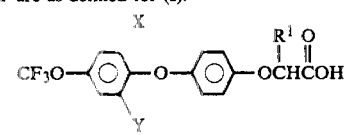

(I)e
$R^1$, X and Y are as defined for (I).

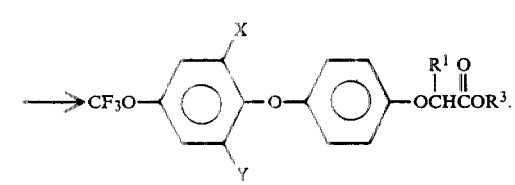

$R^3$ is limited to $Na^+$, $\tfrac{1}{2} Ca^{2+}$ and $N^+R^7R^8R^9R^{10}$
$R^1$, X and Y are as defined for (I).

5. (I)e ⟶ 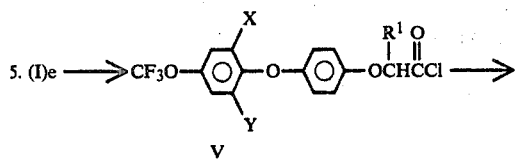 ⟶

V $R^1$, X and Y are as defined for (I).

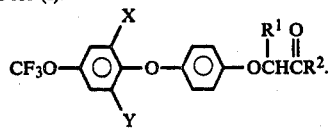

(I)f, $R^2$ is $OR^3$, $NR^4R^5$ or $SR^6$, with $R^6$ limited to alkyl of 1 through 6 carbons
$R^1$, $R^4$, $R^5$, $R^6$, X and Y are as defined for (I).

PROCEDURE 1

The compound IIa with X=Y=H is known [See Zh. Obshch. Khim. 34(6), 1979-1984(1964) or Chem. Abstr. 61, 8217b (1964).]; monohalogenation of this compound with $Cl_2$ or $Br_2$ can be done at low temperatures, e.g., in a range from $-10°$ to $+10°$ C. while the second halogen can be introduced at higher temperatures, e.g., in a range from 45° to 50° C. Pressure is not critical for both halogenation steps since pressure below and above atmospheric are suitable. However, for convenience, atmospheric pressure is preferred. This step is not shown in the schematic.

In the first schematic step a salt of II is generated by use of a base. Fluoro-, chloro-, or bromonitrobenzene can be used as a reactant. The fluoro compound does not require a catalyst, e.g., one containing copper, for the reaction to proceed in a relatively short time period. Addition of the catalyst is generally desirable with the more sluggish reactions, e.g., where either or both of X and Y is halogen, as defined. Generally preferred solvents are dimethylformamide (DMF), dimethylacetamide (DMAC), dimethyl sulfoxide (DMSO), and tetramethylene sulfone (sulfolane).

In the second step the reduction can be done by catalytic hydrogenation, with due care being taken to avoid hydrogenolysis of halogen X or Y, or by the usual chemical reductions, such as with iron and acetic acid.

The third step is a Sandmeyer-type reaction, conducted in the usual manner.

The fourth step is the reaction of the phenolic compound IIIc with the appropriate α-halocarboxylic acid compound in the presence of a base.

PROCEDURE 2

The (trifluoromethoxy)bromobenzene is known [See J. Org. Chem. 29, 3(1964)]. The corresponding iodo compound can be made from the corresponding aniline [J. Org. Chem., loc, cit.]. The first step in the procedure involves reaction of a phenolic compound with the mentioned bromo or iodo compound in the presence of a base in an aprotic solvent (e.g., DMF, DMAC, DMSO, or sulfolane), preferably in the presence of a copper-containing catalyst.

Catalytic hydrogenolysis of IIIe, or cleavage of the benzyl ether by chemical means provides IIId, which is converted to (I)b by reaction with the appropriate α-halocarboxylic acid compound in the presence of a base.

PROCEDURE 3(a)

The chloronitro(trifluoromethoxy)benzene is known [See Zhur. Obsche i Khim. 31, 915-924(1961) or Chem. Abstr. 55, 23409a (1961).]. In the first step this compound reacts with hydroquinone in the presence of a base in an aprotic solvent (such as DMF, DMAC, DMSO or sulfolane) to give IVa. The second step can be done in much the same manner as mentioned for the fourth step of Scheme 1.

PROCEDURE 3(b)

The first step proceeds much as in the first step of procedure 3(a), but without the concern of O,O'-diarylation associated with the use of plain hydroquinone.

In the second step the benzyl ether IVb is cleaved by chemical methods known for cleaving benzyl ethers. The compound IVa can be further reacted as described in the second step of procedure 3(a).

PROCEDURE 3(c)

The compound VIa can be prepared by operations described for similar compounds (See Belgian Pat. No. 848,526). This compound reacts in a manner similar to that described for preparation of IVa and IVb, but gives (I)c directly.

PROCEDURE 4

The ester (I)d can be cleaved by aqueous base or acid to the free acid (I)e, which can be converted to the salt (I)f by treatment with the appropriate base. The ester can be converted directly to the salt if desired by treatment with the appropriate base, in many cases.

PROCEDURE 5

The carboxylic acid (I)e can be converted to the acid chloride V by the usual reagents. The acid chloride reacts with alcohols, mercaptans and amines to provide the esters, thiol esters, and amides of Formula (I)f.

The following examples further illustrate the preparation of compounds of this invention. All parts and percentages are by weight and all temperatures are in degrees Celsius, unless otherwise specified.

EXAMPLE 1

2-[[4-[4-(trifluoromethoxy)phenoxy]phenoxy]]-propanoic acid, methyl ester

To a stirred solution of 35.6 g. (0.2 mole) of 4-(trifluoromethoxy)phenol in 100 ml. of DMF is added 10.8 g. (0.2 mole) of sodium methoxide, followed by 21.2 ml. (0.2 mole) of 4-fluoronitrobenzene. The mixture is heated on a steam bath for 1 hr. Most of the DMF is then removed and the residue treated with methylene chloride and water. The organic layer is washed with dilute caustic, dried, and evaporated to a yellow oil, which is further purified by distillation, providing 50 g. (84%) of 4-[4-(trifluoromethoxy)phenoxy]-1-nitrobenzene, b.p. 130° at 0.1 mm.

The above nitro compound (47.45 g., 0.1586 mole) is reduced in a solution of 285 ml. of acetic acid and 142 ml. of water at 60° to 100° by portionwise addition of 47.6 g. (0.85 mole) of powdered iron. The mixture is stripped of solvent and treated with water, caustic and butyl chloride. The butyl chloride is separated by decantation. The rest of the mixture is steam-distilled and the distillate extracted with butyl chloride. The combined butyl chloride extracts are dried, the solvent removed, and the residue distilled, providing 36.55 g. (86%) of 4-[4-(trifluoromethoxy)phenoxy]aniline, b.p. 122° at 0.2 mm.

The above amino compound (10 g., 0.037 mole) in 45 ml. of acetic acid and 25 ml. of water is treated with 8 ml. of concentrated sulfuric acid. The mixture is treated with an aqueous solution (10 ml.) of 2.6 g. (0.038 mole) of sodium nitrite at 5° to 10° and kept an additional hour in this temperature range. The reaction solution is cautiously added to a solution of 36 ml. of water and 49 ml. of concentrated sulfuric acid at 125° to 135°. After 20 minutes the mixture is cooled to 25°, diluted with 200 ml. of water, and extracted with methylene chloride. The methylene chloride solution is washed with water and with saturated sodium bicarbonate solution, dried, and the solvent removed. The residual oil is distilled at the water pump, with condenser water at 90°, providing 7.3 g. (73%) of oil. The oil solidifies, providing 4-[4-(trifluoromethoxy)phenoxy]phenol as a yellow solid, m.p. 46°–48°.

The above phenolic compound (4.97 g., 0.0184 mole) is treated with 29 ml. of butanone, 2.7 g. of potassium carbonate, and 2.2 ml. (0.02 mole) of methyl 2-bromopropanoate, and the mixture boiled under reflux for a day. The mixture is filtered and the solvent removed. A solution of the residue in methylene chloride is washed with 1N sodium hydroxide, water, and saturated sodium bicarbonate solution, then dried, and the solvent removed to provide, as an oil, 2-[[4-[4-(trifluoromethoxy)phenoxy]phenoxy]]propanoic acid, methyl ester.

EXAMPLE 1b 4-(trifluoromethoxy)-2-chlorophenol

About 2.6 ml. (about 0.057 mole) of liquified chlorine is slowly added to a solution of 10 g. (0.0562 mole) of 4-(trifluoromethoxy)phenol in 40 ml. of carbon tetrachloride at −5° to −10°. After an additional 10 min. at −5° to −10° the solvent is removed under vacuum and the residue distilled at the water pump (about 13 mm pressure), providing 9.97 g. (84%) of 4-(trifluoromethoxy)-2-chlorophenol as a yellow oil, b.p. 65°–68°.

EXAMPLE 2

2-[[4-[4-(trifluoromethoxy)phenoxy]phenoxy]]-propanoic acid, methyl ester

A solution of 10.01 g. (0.05 mole) of 4-(trifluoromethoxy)-1-bromobenzene in 60 ml. of DMF is treated with a solution of 2.70 g. (0.05 mole) of sodium methoxide in a little methanol, followed by 12.05 g. (0.05 mole) of 4-(benzyloxy)phenol and 0.5 g. of cuprous chloride. The mixture is blanketed with nitrogen, the methanol boiled off, and the mixture boiled under reflux for 6 hrs. The mixture is cooled, filtered, and diluted with water, and the product extracted into methylene chloride. The methylene chloride extracts are washed with aqueous sodium chloride, dried, and evaporated to an oil. The oil is distilled (b.p. 155° at 0.2 mm), with use of a 90°–100° condenser; the distillate solidifies, and is recrystallized from methanol, providing 2.89 g. (16%) of 4-[4-(trifluoromethoxy)phenoxy]phenyl benzyl ether, m.p. 69°–71°.

A solution of 2.84 g. (0.00789 mole) of the above benzyl ether compound in 250 ml. of methanol is treated with a catalytic amount of 5% palladium on charcoal. The mixture is hydrogenated at 50 p.s.i. of hydrogen on a shaker apparatus for 3 hrs. The catalyst is filtered off and the solvent removed to leave a residue of 4-[4-(trifluoromethoxy)phenoxy]phenol as a solid, m.p. 44°–46°.

This phenolic compound is converted to 2-[[4-[4-(trifluoromethoxy)phenoxy]phenoxy]]propanoic acid, methyl ester, by the method in Example 1.

EXAMPLE 3

2-[[4-[4-(trifluoromethoxy)-2-nitrophenoxy]phenoxy]]-propanoic acid, methyl ester To a mixture of 10.01 g. of 4-(benzyloxy)phenol and 3.51 g. (0.05 mole) of potassium methoxide in 75 ml. of DMF is added 12.08 g. (0.05 mole) of 4-(trifluoromethoxy)-2-nitro-1-chlorobenzene. The mixture is heated to complete the reaction. Most of the solvent is removed at reduced pressure and the residue treated with methylene chloride and water. The methylene chloride solution is washed with saturated brine, dried, and the solvent removed, leaving 4-[4-(trifluoromethoxy)-2-nitrophenoxy]-phenyl benzyl ether.

The above benzyl ether (10.13 g., 0.025 mole) is stirred with 85 ml. of methylene chloride and cooled to −65°, and 3.7 ml. (0.039 mole) of boron tribromide in 85 ml. of methylene chloride is slowly added. The temperature is allowed to warm to 25°. Water (280 ml.) is added, followed by 560 ml. of ether. The mixture is stirred for 0.5 hr. and the organic layer washed with saturated sodium bicarbonate solution. It is then extracted with two 30-ml. portions of 2N sodium hydroxide and the basic extracts quickly acidified with 2N HCl and extracted with ether. The ether solution on drying and removal of solvent affords a residue of 4-[4-(trifluoromethoxy)-2-nitrophenoxy]phenol.

The above phenol compound (5.66 g., 0.02 mole) is dissolved in 30 ml. of butanone. The solution is treated with 3 g. of potassium carbonate and 2.3 ml. (0.02 mole) of methyl 2-bromopropanoate, then boiled under reflux for a day. The mixture is filtered, the solvent removed and the residue dissolved in methylene chloride. The methylene chloride solution is washed with 1N NaOH, water, and saturated sodium bicarbonate solution. After drying, removal of solvent affords a residue of 2-[[4-[4-(trifluoromethoxy)-2-nitrophenoxy]phenoxy]]-propanoic acid, methyl ester.

EXAMPLE 4

2-[[4-[4-(trifluoromethoxy)-2-nitrophenoxy]phenoxy]]-propanoic acid, methyl ester A solution of 3.92 g. (0.02 mole) of 2-(4-hydroxyphenoxy)propanoic acid, methyl ester in 30 ml. of DMF is treated with 1.4 g. of potassium methoxide, followed by 4.83 g. (0.02 mole) of 4-(trifluoromethoxy)-2-nitro-1-chlorobenzane. The mixture is heated to complete the reaction. Most of the solvent is removed under vacuum, and the residue treated with water and methylene chloride. The methylene chloride solution is washed with saturated brine, dried, and the solvent removed, leaving 2-[[4-[4-(trifluoromethoxy)-2-nitrophenoxy]phenoxy]]-propanoic acid, methyl ester.

EXAMPLE 5

2[[4-[4-(trifluoromethoxy)phenoxy]phenoxy]]-propanoic acid

A solution of 7.13 g. (0.02 mole) of 2-[[4-[4-(trifluoromethoxy)phenoxy]phenoxy]]propanoic acid, methyl ester in 150 ml. of methanol is treated with 20 ml. of 1N sodium hydroxide. The mixture is boiled under reflux to complete the reaction. The solvent is removed, leaving a residue of 2-[[4-[4-(trifluoromethoxy)phenoxy]phenoxy]]propanoic acid, sodium salt. Acidification with dilute sulfuric acid, followed by extraction with methylene chloride, and removal of solvent from the dried methylene chloride solution, provides a residue of 2-[[4-[4-(trifluoromethoxy)phenoxy]phenoxy]]propanoic acid.

Treatment of an equivalent of this acid with an equivalent of an appropriate base, e.g., in a methanol mixture, provides the corresponding salt of the acid.

EXAMPLE 6

2-[[4-[4-(trifluoromethoxy)phenoxy]phenoxy]]propanoyl chloride

To 17.11 g. (0.05 mole) of 2-[[4-[4-(trifluoromethoxy)phenoxy]phenoxy]]propanoic acid is added 1 ml. of DMF, followed by 50 ml. of thionyl chloride. After evolution of HCl ceases, the thionyl chloride excess is removed in vacuum. The residue is extracted with methylene chloride and the methylene chloride solution washed with ice water, dried, and the solvent removed, leaving 2-[[4-[4-(trifluoromethoxy)phenoxy]phenoxy]]-propanoyl chloride.

EXAMPLE 7

2-[[4-[4-(trifluoromethoxy)phenoxy]phenoxy]]-propanoic acid, N-methyl amide

Into a solution of 3.61 g. (0.01 mole) of 2-[[4-[4-(trifluoromethoxy)phenoxy]phenoxy]]propanoyl chloride in 20 ml. of tetrahydrofuran (THF) is passed a stream of gaseous methylamine. When the reaction is over, the solvent is removed and the residue treated with methylene chloride. The methylene chloride solution is washed with water, dried, and the solvent removed, providing a residue of 2-[[4-[4-(trifluoromethoxy)-phenoxy]phenoxy]]propanoic acid, N-methyl amide.

EXAMPLE 8

2-[[4-[4-(trifluoromethoxy)phenoxy]phenoxy]]-propanoic acid, thiolmethyl ester

To a solution of 3.61 g. (0.01 mole) of 2-[[4-[4-(trifluoromethoxy)phenoxy]phenoxy]]propanoyl chloride in 20 ml. of THF at 0° to 5° is added 0.6 ml. of liquid methyl mercaptan, followed by 0.9 ml. of pyridine. The mixture is stirred cold for a few minutes, then warmed to 30°. The solvent is removed, the residue treated with methylene chloride, and the methylene chloride solution washed with water and dried. Removal of the solvent leaves a residue of 2-[[4-[4-(trifluoromethoxy)-phenoxy]phenoxy]]propanoic acid, thiolmethyl ester.

The 4-(trifluoromethoxy)phenyl phenyl ethers of this invention can be prepared by suitable application of the methods of the previous examples to the appropriate starting materials. Some exemplary compounds which can be thus prepared are listed in Table 1.

TABLE I $$CF_3O-\underset{Y}{\overset{X}{\underset{|}{\bigcirc}}}-O-\bigcirc-O-\underset{R^2}{\overset{R^1\ O}{\underset{|}{C}H}CR^2}$$

| X | Y | $R^1$ | $R^2$ |
|---|---|---|---|
| H | H | H | —$OCH_3$ |
| H | H | $CH_3$ | —$OCH_3$ |
| H | H | $C_2H_5$ | —$OCH_3$ |
| Cl | H | $CH_3$ | —$OCH_3$ |
| Br | H | $CH_3$ | —$OCH_3$ |
| $NO_2$ | H | $CH_3$ | —$OCH_3$ |
| Cl | Cl | $CH_3$ | —$OCH_3$ |
| H | H | $CH_3$ | —OH |
| H | H | $CH_3$ | —$OC_2H_5$ |
| H | H | $CH_3$ | —$O(CH_2)_5CH_3$ |
| H | H | $CH_3$ | —$O^\ominus Na^\oplus$ |
| H | H | $CH_3$ | —$O^\ominus K^\oplus$ |
| H | H | $CH_3$ | —$O^\ominus (\tfrac{1}{2}\ Ca^{2+})$ |
| H | H | $CH_3$ | —$O^\ominus H_3\overset{\oplus}{N}CH_3$ |
| H | H | $CH_3$ | —$O^\ominus H_3\overset{\oplus}{N}(CH_2)_{11}CH_3$ |
| H | H | $CH_3$ | —$O^\ominus H_3\overset{\oplus}{N}CH_2CH_2OH$ |
| H | H | $CH_3$ | —$O^\ominus H_3\overset{\oplus}{N}\overset{|}{C}HCH_2CH_3$ with $CH_2OH$ |
| H | H | $CH_3$ | —$O^\ominus H_3\overset{\oplus}{N}(CH_2)_3CH_3$ |
| H | H | $CH_3$ | —$O^\ominus H_2\overset{\oplus}{N}(CH_3)_2$ |
| H | H | $CH_3$ | —$O^\ominus H\overset{\oplus}{N}(CH_3)_3$ |
| H | H | $CH_3$ | —$O^\ominus H\overset{\oplus}{N}(CH_2CH_2OH)_3$ |
| H | H | $CH_3$ | —$O^\ominus(CH_3)_3\overset{\oplus}{N}CH_2-\bigcirc$ |
| H | H | $CH_3$ | $NH_2$ |
| H | H | $CH_3$ | $NHCH_3$ |
| H | H | $CH_3$ | —$NH(CH_2)_3CH_3$ |
| H | H | $CH_3$ | —$N(CH_3)_2$ |
| H | H | $CH_3$ | $CH_3NOCH_3$ |
| H | H | $CH_3$ | —$SCH_3$ |
| H | H | $CH_3$ | —S—(n-$C_6H_{13}$) |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |

-continued

|  | Percent by Weight | | |
| --- | --- | --- | --- |
|  | Active Ingredient | Diluent(s) | Surfactant(s) |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvent Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 7, line 62 and Ex. 8, 12, 15, 39, 41, 52, 53, 58, 132, 138–40, 162–164, 166, 167, 169–182.

H. Gysin and E. Knüsli, U.S. Pat. No. 2,891,855, June 23, 1959, col. 3, line 66 through Col. 5, line 17 Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Edn. Blackwell Scientific Publications, Oxford, 1968, pp. 101–103.

A. Wettable Powder

| 2-[[4-[4-(trifluoromethyloxy)phenoxy]phenoxy]]-propanoic acid, methyl ester | 35% |
| --- | --- |
| hydrous calcium silicate | 61% |
| sodium liquinsulfonate | 3% |
| sodium dioctylsulfosuccinate | 1% |

The ingredients are thoroughly blended, passed through a hammer mill and sifted through a U.S.S. No. 50 sieve (0.3mm openings) before packaging.

All compounds of the invention can be formulated in similar manner.

B. Solution

| 2-[[4-[2-chloro-4-(trifluoromethoxy)phenoxy]-phenoxy]]propanoic acid, methyl ester | 50% |
| --- | --- |
| dimethylformamide | 50% |

The ingredients are stirred together to make a solution for direct low-volume application.

C. Granule

| Solution of Example B | 10% |
| --- | --- |
| attapulgite granules (0.71/0.30mm) | 90% |

The solution is sprayed upon the preformed clay granules in a double cone blender.

D. Emulsifiable Concentrate

| 2-[[4-[4-(trifluoromethyloxy)phenoxy]phenoxy]]-propanoic acid, methyl ester | 30% |
| --- | --- |
| blend of oil soluble sulfonates and polyoxyethylene ethers | 6% |
| cyclohexanone | 64% |

The ingredients are combined and stirred with gentle warming to speed mixing. A fine-screen filter is included in the packaging operation to remove any extraneous undissolved material.

Compositions can contain, in addition to the active ingredients of this invention, other conventional agricultural chemicals such as fertilizers, plant growth modifiers or herbicides.

For example, the compounds of Formula I can be combined with the following herbicides:

(1) 5-tert-butyl-3-(2,4-dichloro-5-isopropoxyphenyl)-1,3,4-oxadiazol-2-one;
(2) 6-methylthio-2,4-bis(ethylamino)-s-triazine;
(3) 3-isopropyl-(1H)-benzo-2,1,3-thiodiazin-4-one-2,2-dioxide;
(4) 2,4-dichlorophenoxyacetic acid and related esters and salts.

Combinations with wheat herbicides:

(1) 2,4-dichlorophenoxyacetic acid and related esters and salts;
(2) S-(2,2,3-trichloroallyl)-diisopropylthiocarbamate;
(3) Methyl 2-[4-(2,4-dichlorophenoxy(phenoxy)]-propanoate;
(4) 1,2-dimethyl-3,5-diphenyl-1H-pyrazolium methyl sulfate;
(5) 4-chloro-2-butynyl 3-chlorocarbanilate.

The compounds of Formula I can also be combined with other herbicides and are particularly useful in combination with bromacil [3-(sec-butyl)-5-bromo-6- methyluracil], diuron [3-(3,4-dichlorophenyl)-1,1-dimethylurea], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido)-phenyl tert-butylcarbamate, 2-methyl-4-chlorophenoxyacetic acid, its salts or esters, 4-amino-6-tert-butyl-3-methylthioas-triazin-5(4H)-one, and linuron [3-(3,4-dichlorophenyl)-1-methoxy-1-methyl urea] for controlling a broad spectrum of weeds.

The agricultural chemicals listed above are exemplary of the compounds which can be mixed with the active compounds and are not intended to limit the invention in any way.

USE

The compounds of the present invention are useful when applied as pre- and/or post-emergence treatments for broad-spectrum control of a wide variety of weed and brush species growing on industrial sites, storage lots, along fences and building foundations, along railroad and utility rights-of-way, etc. In addition, the compounds of the invention have utility for weed control in certain crops, such as soybeans.

The precise amount of the compounds of this invention to be used in any particular situation will vary widely according to the end result desired. Factors affecting the optimum rate of application include the plant species to be controlled, soil type, formulation used, prevailing weather conditions, foliage density, length of time for which residual activity is desired, etc. Broadly speaking, the compounds are used at levels of about 0.125 to 20 kilograms per hectare, preferably approximately 0.25 to 10 kilograms per hectare. In general, the higher rates of application from within this range will be selected for adverse conditions or where extended persistence in soil is desired, and the lower rates for weed control in crops.

Herbicidal activity of the subject compounds was discovered in greenhouse tests. The test procedures and the results obtained are described below.

TEST I

Seeds of crabgrass (Digitaria spp.), barnyardgrass (*Echinochloa crusgalli*), wild oats (*Avena fatua*), *Cassia tora*, morningglory (Ipomoea spp.), cocklebur (Xanthium spp.), sorghum, corn, soybean, rice, wheat and nutsedge tubers were planted in a growth medium and treated preemergence with the chemicals dissolved in a nonphytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings: B=burn; G=growth retardation; C=chlorosis/necrosis; U=unusual pigmentation; E=emergence inhibition; and H=formative effects. The ratings for the compound tested by this procedure are shown in Table II.

TABLE II

POST EMERGENCE

| COMPOUND | kg/ha | Bush Beans | Cotton | Sorghum | Corn | Soybean | Wheat | Wild Oats | Rice | Barnyard-grass | Crabgrass | Morning Glory | Cocklebur | Cassia | Nutsedge |
|---|---|---|---|---|---|---|---|---|---|---|---|---|---|---|---|
| CF$_3$O—⟨○⟩—O—⟨○⟩—OCHCOCH$_3$ with CH$_3$ and =O | 2 | 2H | 1B 1H | 10C | 10C | 2C | 10C | 10C | 10C | 10C | 10C | 5C | 7C | 10C | 1C 5G |
| | 0.4 | 0 | 0 | 10C | 10C | 4G 0 | 9C | 10C | 10C | 10C | 10C | 2C | 2C | 0 | 0 |

PRE-EMERGENCE

| COMPOUND | kg/ha | Sorghum | Corn | Soybean | Wheat | Wild oats | Rice | Barnyardgrass | Crabgrass | Morning Glory | Cocklebur | Cassia | Nutsedge |
|---|---|---|---|---|---|---|---|---|---|---|---|---|---|
| CF$_3$O—⟨○⟩—O—⟨○⟩—OCHCOCH$_3$ with CH$_3$ and =O | 2 | 10E 3C 9G | 10H 7U 9G | 0 | 9H 2C 9G | 9H 3C 9G | 10E 9G | 10E 10E | 10E 10E | 2G | 0 | 0 | 0 |
| | 0.4 | | | 0 | | | | | | — | 0 | 0 | 0 |

TEST II

Two plastic bulb pans were filled with fertilized and limed Fallsington silt loam soil. One pan was planted with corn, sorghum and several grassy weeds. The other pan was planted with soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), cocklebur (*Xanthium pennsylvanicum*), pigweed (*Amaranthus retroflexus*), morningglory (*Ipomoea hederacea*), cassia (*Cassia tora*), velvetleaf (*Abutilon theophrasti*), and jimsonweed (*Datura stramonium*). In addition, a 5-inch diameter paper pot was filled with prepared soil and planted with rice and wheat. Another 5-inch pot was planted with sugarbeets. The above four containers were treated preemergence (compound sprayed on soil surface before seed germination) with the test chemical dissolved in a non-phytotoxic solvent.

Twenty-eight days after treatment, the plants were evaluated in accordance with the rating system as described above for Test I. The data are summarized in Table III.

"Consisting essentially of" is intended to have its customary meaning: namely, that all specified materials and conditions are very important in practicing the invention but that unspecified materials and conditions are not excluded so long as they do not prevent the benefits of the invention from being realized.

What is claimed:

1. A compound of the formula

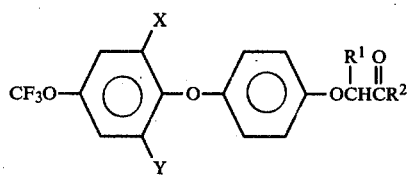

wherein
- $R^1$ is H, $CH_3$ or $CH_3CH_2$;
- $R^2$ is $OR^3$, $NR^4R^5$, or $SR^6$;
- $R^3$ is H, alkyl of one through six carbons, $Na^\oplus$, $K^\oplus$, $Ca^{+2}$ or $\oplus NR^7R^8R^9R^{10}$;
- $R^4$ is H, or $CH_3$;
- $R^5$ is H, alkyl of one through four carbons or $OCH_3$;
- $R^6$ is alkyl of one through six carbons;
- $R^7$, $R^8$, and $R^9$ can be the same or different and each can be hydrogen, alkyl of one through four carbon atoms or hydroxyalkyl of two through four carbon atoms;
- $R^{10}$ is hydrogen, alkyl of one through twelve carbon atoms or benzyl;
- provided that when $R^5$ is $OCH_3$, $R^4$ is $CH_3$;
- X is H, Cl, Br or $NO_2$; and
- Y is H or Cl;
- provided that when Y is Cl, X must be H or Cl.

2. The compound of claim 1 wherein $R^1$ is $CH_3$.
3. The compound of claim 1 wherein $R^2$ is $OR^3$.
4. The compound of claim 1 wherein $R^3$ is $CH_3$ or $CH_3CH_2$.
5. The compound of claim 1 wherein X is H or Cl.
6. The compound of claim 1 wherein Y is H.
7. The compound of claim 1 wherein
- $R^1$ is $CH_3$;
- $R^2$ is $OR^3$;
- $R^3$ is $CH_3$ or $CH_3CH_2$;
- X is H or Cl;
- Y is H.

8. The compound of claim 1 which is 2-[[4-[4-(trifluoromethoxyl)phenoxy]phenoxy]]propanoic acid, methyl ester.

9. The compound of claim 1 which is 2-[[4-[2-chloro-4-(trifluoromethoxy)phenoxy]phenoxy]]propanoic acid methyl ester.

10. An agricultural composition consisting essentially of a diluent, surfactant or a mixture thereof and a compound of claim 1.

11. An agricultural composition consisting essentially of a diluent, surfactant or a mixture thereof and a compound of claim 2.

12. An agricultural composition consisting essentially of a diluent, surfactant or a mixture thereof and a compound of claim 3.

13. An agricultural composition consisting essentially of a diluent, surfactant or a mixture thereof and a compound of claim 4.

14. An agricultural composition consisting essentially of a diluent, surfactant or a mixture thereof and a compound of claim 5.

15. An agricultural composition consisting essentially of a diluent, surfactant or a mixture thereof and a compound of claim 6.

16. An agricultural composition consisting essentially of a diluent, surfactant or a mixture thereof and a compound of claim 7.

17. An agricultural composition consisting essentially of a diluent, surfactant or a mixture thereof and a compound of claim 8.

18. An agricultural composition consisting essentially of a diluent, surfactant or a mixture thereof and a compound of claim 9.

19. A method for control of weeds which comprises applying to a locus to be protected an effective herbicidal amount of a compound of claim 1.

20. A method for control of weeds which comprises applying to a locus to be protected an effective herbicidal amount of a compound of claim 2.

21. A method for control of weeds which comprises applying to a locus to be protected an effective herbicidal amount of a compound of claim 3.

22. A method for control of weeds which comprises applying to a locus to be protected an effective herbicidal amount of a compound of claim 4.

23. A method for control of weeds which comprises applying to a locus to be protected an effective herbicidal amount of a compound of claim 5.

24. A method for control of weeds which comprises applying to a locus to be protected an effective herbicidal amount of a compound of claim 6.

25. A method for control of weeds which comprises applying to a locus to be protected an effective herbicidal amount of a compound of claim 7.

26. A method for control of weeds which comprises applying to a locus to be protected an effective herbicidal amount of a compound of claim 8.

27. A method for control of weeds which comprises applying to a locus to be protected an effective herbicidal amount of a compound of claim 9.

* * * * *